US008435474B2

(12) United States Patent
Fomitchev et al.

(10) Patent No.: US 8,435,474 B2
(45) Date of Patent: May 7, 2013

(54) SURFACE-TREATED METAL OXIDE PARTICLES

(75) Inventors: Dmitry Fomitchev, Lexington, MA (US); Joachim K. Floess, Urbana, IL (US); William R. Williams, Reading, MA (US)

(73) Assignee: Cabot Corporation, Boston, MA (US)

( * ) Notice: Subject to any disclaimer, the term of this patent is extended or adjusted under 35 U.S.C. 154(b) by 921 days.

(21) Appl. No.: 11/774,478

(22) Filed: Jul. 6, 2007

(65) Prior Publication Data

US 2008/0070140 A1    Mar. 20, 2008

Related U.S. Application Data

(60) Provisional application No. 60/844,828, filed on Sep. 15, 2006.

(51) Int. Cl.
| C01B 33/00 | (2006.01) |
| C01B 33/12 | (2006.01) |
| B32B 5/16 | (2006.01) |
| B32B 9/00 | (2006.01) |
| B32B 15/02 | (2006.01) |
| B32B 17/02 | (2006.01) |
| B32B 19/00 | (2006.01) |
| B32B 21/02 | (2006.01) |
| B32B 23/02 | (2006.01) |
| B32B 27/02 | (2006.01) |

(52) U.S. Cl.
USPC .......................... 423/324; 423/335; 428/405

(58) Field of Classification Search .................. None
See application file for complete search history.

(56) References Cited

U.S. PATENT DOCUMENTS

| 3,900,588 A | 8/1975 | Fisher |
| 4,845,004 A | 7/1989 | Kobayashi |
| 4,923,520 A | 5/1990 | Anzai et al. |
| 4,943,507 A | 7/1990 | Takahashi et al. |
| 4,950,502 A * | 8/1990 | Saam et al. .......... 427/213.36 |
| 4,985,477 A | 1/1991 | Collins et al. |
| 5,008,305 A | 4/1991 | Kennan et al. |
| 5,009,874 A | 4/1991 | Parmentier et al. |
| 5,013,585 A | 5/1991 | Shimizu et al. |
| 5,024,915 A | 6/1991 | Sato et al. |
| 5,039,736 A | 8/1991 | Fujiki |
| 5,096,733 A | 3/1992 | Vallyathan et al. |
| 5,135,832 A | 8/1992 | Sacripante et al. |
| 5,194,356 A | 3/1993 | Sacripante et al. |
| 5,226,930 A | 7/1993 | Sasaki |
| 5,266,432 A | 11/1993 | Hayashi et al. |
| 5,320,925 A | 6/1994 | Imai et al. |
| 5,376,172 A | 12/1994 | Tripp et al. |
| 5,415,936 A | 5/1995 | Deusser et al. |
| 5,422,214 A | 6/1995 | Akiyama et al. |
| 5,424,161 A | 6/1995 | Hayashi et al. |
| 5,475,044 A | 12/1995 | Stein |
| 5,480,755 A | 1/1996 | Uchiyama et al. |
| 5,484,678 A | 1/1996 | Pickering et al. |
| 5,531,929 A | 7/1996 | Kobayashi |
| 5,543,173 A | 8/1996 | Horn, Jr. et al. |
| 5,597,853 A | 1/1997 | Itoh et al. |
| 5,651,921 A | 7/1997 | Kaijou |
| 5,665,156 A | 9/1997 | Ettlinger et al. |
| 5,665,511 A | 9/1997 | Imai et al. |
| 5,686,054 A | 11/1997 | Barthel et al. |
| 5,711,797 A | 1/1998 | Ettlinger et al. |
| 5,716,748 A | 2/1998 | Hasegawa et al. |
| 5,725,987 A | 3/1998 | Combes et al. |
| 5,747,211 A | 5/1998 | Hagi et al. |
| 5,766,814 A | 6/1998 | Baba et al. |
| 5,776,240 A | 7/1998 | Deller et al. |
| 5,776,646 A | 7/1998 | Hagi et al. |
| 5,824,442 A | 10/1998 | Tanikawa et al. |
| 5,824,739 A | 10/1998 | Kondo et al. |
| 5,827,632 A | 10/1998 | Inaba et al. |
| 5,840,287 A | 11/1998 | Guskey et al. |
| 5,843,525 A | 12/1998 | Shibasaki et al. |
| 5,849,451 A | 12/1998 | Ishihara et al. |
| 5,900,315 A | 5/1999 | Little |
| 5,902,635 A | 5/1999 | Garafalo et al. |
| 5,908,660 A | 6/1999 | Griffith et al. |
| 5,916,722 A | 6/1999 | Creatura et al. |
| 5,919,298 A | 7/1999 | Griffith et al. |
| 5,942,590 A | 8/1999 | Burns et al. |
| 5,959,005 A | 9/1999 | Hartmann et al. |
| 5,969,023 A | 10/1999 | Enami et al. |
| 5,989,768 A | 11/1999 | Little |
| 6,004,711 A | 12/1999 | Bourne et al. |

(Continued)

FOREIGN PATENT DOCUMENTS

| CN | 1688509 A | 10/2005 |
| DE | 196 16 781 A1 | 11/1997 |

(Continued)

OTHER PUBLICATIONS

Chen et al., *Journal of Colloid and Interface Science*, 281: 339-350 (2005).

Maciel et al., "Silicon-29 NMR study of the surface of silica gel by cross polarization and magic-angle spinning," *J. Am. Chem. Soc.*, 102 (25): 7606-7607 (Dec. 3, 1980).

Sindorf et al., "Cross-polarization/magic-angle spinning silicon-29 nuclear magnetic resonance study of silica gel using trimethylsilane bonding as a probe of surface geometry and reactivity," *J. Phys. Chem.*, 86 (26): 5208-5219 (Dec. 23, 1982).

Sindorf et al., "Solid-state NMR studies of the reactions of silica surfaces with polyfunctional chloromethylsilanes and ethoxymethylsilanes," *J. Am. Chem. Soc.*, 105 (12): 3767-3776 (Jun. 15, 1983).

Yoshida, "Silica nucleation, polymerization, and growth preparation of monodispersed sols," in *Coloidal Silica: Fundamentals and Applications* (Bergna et al., eds.), Chapter 6, 47-56 (CRC Press, an imprint of the Taylor & Francis Group, Boca Raton, Florida, 2006).

(Continued)

*Primary Examiner* — Emily Le
*Assistant Examiner* — Michael Forrest

(57) ABSTRACT

The invention provides metal oxide particles surface-treated with at least one alkoxysilane compound, methods of making such, and toners comprising same.

19 Claims, 2 Drawing Sheets

U.S. PATENT DOCUMENTS

| | | | |
|---|---|---|---|
| 6,004,714 A | 12/1999 | Ciccarelli et al. | |
| 6,015,843 A | 1/2000 | Van Vlasselaer et al. | |
| 6,025,455 A | 2/2000 | Yoshitake et al. | |
| 6,045,650 A | 4/2000 | Mitchnick et al. | |
| 6,051,672 A | 4/2000 | Burns et al. | |
| 6,066,421 A | 5/2000 | Julien et al. | |
| 6,077,640 A | 6/2000 | Komai et al. | |
| 6,086,668 A | 7/2000 | Farneth et al. | |
| 6,087,059 A | 7/2000 | Duggan et al. | |
| 6,103,441 A | 8/2000 | Tomita et al. | |
| 6,107,351 A | 8/2000 | Burns et al. | |
| 6,165,663 A | 12/2000 | Baba et al. | |
| 6,180,076 B1 | 1/2001 | Uhrlandt et al. | |
| 6,183,867 B1 | 2/2001 | Barthel et al. | |
| 6,184,408 B1 | 2/2001 | Burns et al. | |
| 6,190,815 B1 | 2/2001 | Ciccarelli et al. | |
| 6,191,122 B1 | 2/2001 | Lux et al. | |
| 6,193,795 B1 | 2/2001 | Nargiello et al. | |
| 6,197,384 B1 | 3/2001 | Schubert et al. | |
| 6,197,470 B1 | 3/2001 | Tamura | |
| 6,203,960 B1 | 3/2001 | Ciccarelli et al. | |
| 6,214,507 B1 | 4/2001 | Sokol et al. | |
| 6,242,147 B1 | 6/2001 | Anno et al. | |
| 6,248,495 B1 | 6/2001 | Inokuchi et al. | |
| 6,255,373 B1 | 7/2001 | Akamatsu et al. | |
| 6,270,937 B2 | 8/2001 | Yuasa et al. | |
| 6,287,739 B1 | 9/2001 | Kawakami et al. | |
| 6,294,303 B1 | 9/2001 | Putnam et al. | |
| 6,312,861 B1 | 11/2001 | Ciccarelli et al. | |
| 6,316,155 B1 | 11/2001 | Kudo et al. | |
| 6,318,124 B1 | 11/2001 | Rutherford et al. | |
| 6,319,647 B1 | 11/2001 | Gutman et al. | |
| 6,335,139 B1 | 1/2002 | Gambayashi et al. | |
| 6,374,637 B1 * | 4/2002 | Costa et al. | 65/17.2 |
| 6,376,077 B1 | 4/2002 | Hiraishi et al. | |
| 6,379,856 B2 | 4/2002 | Sokol et al. | |
| 6,384,125 B1 | 5/2002 | Bergstrom et al. | |
| 6,403,271 B1 | 6/2002 | Suzuki et al. | |
| 6,420,456 B1 | 7/2002 | Koski | |
| 6,448,331 B1 | 9/2002 | Ioka et al. | |
| 6,465,670 B2 | 10/2002 | Thise et al. | |
| 6,479,206 B1 | 11/2002 | Suzuki et al. | |
| 6,489,075 B2 | 12/2002 | Suzuki et al. | |
| 6,503,677 B1 | 1/2003 | Gutman et al. | |
| 6,521,290 B1 | 2/2003 | Kudo et al. | |
| 6,555,282 B2 | 4/2003 | Okuno et al. | |
| 6,573,018 B2 | 6/2003 | Ishibashi et al. | |
| 6,579,929 B1 * | 6/2003 | Cole et al. | 524/492 |
| 6,589,703 B2 | 7/2003 | Stelter et al. | |
| 6,610,777 B1 | 8/2003 | Anderson et al. | |
| 6,613,491 B2 | 9/2003 | Inoue et al. | |
| 6,657,001 B1 | 12/2003 | Anderson et al. | |
| 6,677,095 B2 | 1/2004 | Murota et al. | |
| 6,686,110 B2 | 2/2004 | Kadota | |
| 6,696,212 B2 | 2/2004 | Marsh et al. | |
| 6,706,398 B1 | 3/2004 | Revis | |
| 6,706,457 B2 | 3/2004 | Koumura | |
| 6,736,891 B1 | 5/2004 | Bice et al. | |
| 6,780,559 B2 | 8/2004 | Veregin et al. | |
| 6,800,413 B2 | 10/2004 | Barthel et al. | |
| 6,803,408 B2 | 10/2004 | Anderson et al. | |
| 6,811,856 B2 | 11/2004 | Nun et al. | |
| 6,830,811 B2 | 12/2004 | Chao | |
| 6,840,992 B2 | 1/2005 | Glaum et al. | |
| 6,855,759 B2 | 2/2005 | Kudo et al. | |
| 6,890,657 B2 | 5/2005 | Pickering et al. | |
| 6,899,948 B2 | 5/2005 | Zhang et al. | |
| 6,899,951 B2 | 5/2005 | Panz et al. | |
| 6,972,301 B2 | 12/2005 | Hurlburt et al. | |
| 7,014,969 B2 | 3/2006 | Yachi et al. | |
| 7,014,975 B2 | 3/2006 | Barthel et al. | |
| 7,022,375 B2 | 4/2006 | Schachtely et al. | |
| 7,081,234 B1 | 7/2006 | Qi et al. | |
| 7,083,770 B2 | 8/2006 | Shibasaki et al. | |
| 7,169,832 B2 | 1/2007 | Poppe et al. | |
| 7,186,440 B2 | 3/2007 | Yoshitake et al. | |
| 7,214,459 B2 | 5/2007 | Iizuka et al. | |
| 7,238,387 B2 | 7/2007 | Ogawa et al. | |
| 7,252,885 B2 | 8/2007 | Pickering et al. | |
| 7,262,233 B2 | 8/2007 | Isarov et al. | |
| 7,300,734 B2 | 11/2007 | McDougall et al. | |
| 7,312,009 B2 | 12/2007 | Lee et al. | |
| 7,316,881 B2 | 1/2008 | Rimai et al. | |
| 7,341,625 B2 | 3/2008 | Amirzadeh-Asl | |
| 7,422,834 B2 | 9/2008 | Akiyama et al. | |
| 7,713,326 B2 | 5/2010 | Carstens et al. | |
| 7,799,870 B2 | 9/2010 | Hergenrother et al. | |
| 2002/0037936 A1 * | 3/2002 | Michael et al. | 516/111 |
| 2003/0035888 A1 | 2/2003 | Eriyama et al. | |
| 2003/0082090 A1 | 5/2003 | Blume et al. | |
| 2004/0077768 A1 | 4/2004 | Greenwood | |
| 2004/0102529 A1 | 5/2004 | Campbell et al. | |
| 2004/0138343 A1 | 7/2004 | Campbell et al. | |
| 2005/0011409 A1 | 1/2005 | Isobe | |
| 2005/0014894 A1 | 1/2005 | Flannigan et al. | |
| 2005/0026060 A1 | 2/2005 | Ogawa et al. | |
| 2005/0026087 A1 | 2/2005 | Keller | |
| 2005/0026089 A1 | 2/2005 | Ogawa et al. | |
| 2005/0089353 A1 | 4/2005 | Pickering et al. | |
| 2005/0095521 A1 | 5/2005 | Rimai et al. | |
| 2005/0095522 A1 | 5/2005 | Goebel et al. | |
| 2005/0113488 A1 | 5/2005 | Isarov et al. | |
| 2005/0147908 A1 | 7/2005 | Yamane et al. | |
| 2005/0154124 A1 | 7/2005 | Yoshitake et al. | |
| 2005/0164109 A1 | 7/2005 | Iizuka et al. | |
| 2005/0170109 A1 | 8/2005 | Chen et al. | |
| 2005/0187334 A1 | 8/2005 | Blume et al. | |
| 2005/0203214 A1 | 9/2005 | Amano et al. | |
| 2005/0241531 A1 * | 11/2005 | Meyer et al. | 106/490 |
| 2006/0041035 A1 | 2/2006 | Poppe et al. | |
| 2006/0046178 A1 | 3/2006 | Akiyama et al. | |
| 2006/0062941 A1 | 3/2006 | Bi et al. | |
| 2006/0084746 A1 | 4/2006 | Bice et al. | |
| 2006/0099129 A1 | 5/2006 | Stenzel et al. | |
| 2006/0112860 A1 | 6/2006 | Yoshitake et al. | |
| 2006/0115405 A1 | 6/2006 | Konya et al. | |
| 2006/0121381 A1 | 6/2006 | McDougall et al. | |
| 2006/0121382 A1 | 6/2006 | Choi et al. | |
| 2006/0127787 A1 | 6/2006 | Lee et al. | |
| 2006/0150527 A1 | 7/2006 | Ohara et al. | |
| 2006/0160008 A1 | 7/2006 | Lee et al. | |
| 2006/0171872 A1 | 8/2006 | Adams | |
| 2006/0178451 A1 | 8/2006 | Weller | |
| 2006/0188722 A1 | 8/2006 | White et al. | |
| 2006/0217473 A1 | 9/2006 | Hergenrother et al. | |
| 2006/0225615 A1 | 10/2006 | Raman et al. | |
| 2006/0281009 A1 | 12/2006 | Boyer et al. | |
| 2007/0009823 A1 | 1/2007 | Skorokhod et al. | |
| 2007/0048643 A1 | 3/2007 | Kmiecik-Lawrynowicz et al. | |
| 2007/0148577 A1 | 6/2007 | Ogawa et al. | |
| 2008/0069753 A1 | 3/2008 | Floess et al. | |
| 2008/0070143 A1 | 3/2008 | Fomitchev et al. | |
| 2008/0070146 A1 | 3/2008 | Fomitchev et al. | |

FOREIGN PATENT DOCUMENTS

| | | |
|---|---|---|
| EP | 0 371 147 B1 | 6/1990 |
| EP | 0 694 576 A1 | 1/1996 |
| EP | 0 704 769 A1 | 5/1996 |
| EP | 0 982 268 A1 | 3/2000 |
| EP | 1 559 750 A2 | 8/2005 |
| EP | 1 580 019 A1 | 9/2005 |
| EP | 1 559 750 A3 | 10/2005 |
| EP | 1 591 490 A2 | 11/2005 |
| EP | 1 657 283 A1 | 5/2006 |
| EP | 1 696 006 A1 | 8/2006 |
| JP | 58-216252 A | 12/1983 |
| JP | 62-227160 A | 10/1987 |
| JP | 02-017932 A | 1/1990 |
| JP | 3-187913 A | 8/1991 |
| JP | 4-106184 A | 4/1992 |
| JP | 04-269763 A | 9/1992 |
| JP | 6-100313 A | 4/1994 |
| JP | 06-194863 A | 7/1994 |
| JP | 06-242630 A | 9/1994 |
| JP | 07-064318 A | 3/1995 |
| JP | 7-187647 A | 7/1995 |
| JP | 08-095285 A | 4/1996 |

| | | |
|---|---|---|
| JP | 08-119619 A | 5/1996 |
| JP | 8-245835 A | 9/1996 |
| JP | 10-25427 A | 1/1998 |
| JP | 10-36705 A | 2/1998 |
| JP | 11-246210 A | 9/1999 |
| JP | 2000-044226 A | 2/2000 |
| JP | 2000-258955 A | 9/2000 |
| JP | 2001-031843 A | 2/2001 |
| JP | 2001-097710 A | 4/2001 |
| JP | 2002-029730 A | 1/2002 |
| JP | 2002-146233 A | 5/2002 |
| JP | 2002-244340 A | 8/2002 |
| JP | 2002-256170 A | 9/2002 |
| JP | 2002-275356 A | 9/2002 |
| JP | 2002-338230 A | 11/2002 |
| JP | 2003-137528 A | 5/2003 |
| JP | 2003-201112 A | 7/2003 |
| JP | 2003-238141 A | 8/2003 |
| Jp | 2004-029699 A | 1/2004 |
| JP | 2004-168559 A | 6/2004 |
| JP | 2004-258265 A | 9/2004 |
| JP | 2004-359476 A | 12/2004 |
| JP | 2005-003726 A | 1/2005 |
| JP | 2005-215491 A | 8/2005 |
| JP | 2006-022316 A | 1/2006 |
| JP | 2006-053458 A | 2/2006 |
| JP | 2006-096641 A | 4/2006 |
| JP | 2006-169096 A | 6/2006 |
| JP | 2006-171017 A | 6/2006 |
| JP | 2007-034223 A | 2/2007 |
| JP | 2007-034224 A | 2/2007 |
| WO | 2004/035473 A1 | 4/2004 |
| WO | WO 2004/031076 A1 | 4/2004 |
| WO | WO 2005/095525 A1 | 10/2005 |
| WO | WO 2006/045012 A2 | 4/2006 |
| WO | WO 2006/053632 A2 | 5/2006 |
| WO | WO 2006/116887 A1 | 11/2006 |
| WO | WO 2007013388 A1 | 2/2007 |
| WO | 2008/008287 | 1/2010 |
| WO | 2008/008292 | 1/2010 |
| WO | 2008/008293 | 1/2010 |

OTHER PUBLICATIONS

Caravajal et al., "Structural Characterization of (3-Aminopropyl)triethoxysilane-Modified Silicas by Silicon-29 and Carbon-13 Nuclear Magnetic Resonance," *Analytical Chemistry*, 60(17): 1776-1786 (Sep. 1, 1988).
European Patent Office, International Search Report in International Patent Application No. PCT/US2007/020007 (Mar. 6, 2008).
European Patent Office, International Search Report in International Patent Application No. PCT/US2008/008287 (Oct. 21, 2008).
European Patent Office, International Search Report in International Patent Application No. PCT/US2008/008292 (Nov. 14, 2008).
European Patent Office, International Search Report in International Patent Application No. PCT/US2008/008293 (Oct. 21, 2008).
European Patent Office, International Preliminary Report on Patentability in International Patent Application No. PCT/US2007/020007 (Mar. 17, 2009).
European Patent Office, International Preliminary Report on Patentability in International Patent Application No. PCT/US2008/008287 (Jan. 12, 2010).
European Patent Office, International Preliminary Report on Patentability in International Patent Application No. PCT/US2008/008292 (Jan. 12, 2010).
European Patent Office, International Preliminary Report on Patentability in International Patent Application No. PCT/US2008/008293 (Jan. 12, 2010).
Evonik Industries, Aerosil Product Overview (Evonik Degussa GmbH, 2009).
Garcia et al., "Use of $p$-Toluenesulfonic Acid for the Controlled Grafting of Alkoxysilanes onto Silanol Containing Surfaces: Preparation of Tunable Hydrophillic, Hydrophobic, and Super-Hydrophobic Silica," *J. Am. Chem. Soc.*, 129: 5052-5060 (2007).
Patent Office of the People'S Republic of China, Office Action in Chinese Patent Application No. 200780034354.6 (Nov. 30, 2011).
Gomis et al., "LLE, VLE and VLLE data for the water-n-butanol-n-hexane system at atmospheric pressure," *Fluid Phase Equilibria*, 316: 135-140 (2012).
Cabot Corporation, CAB-O-SIL TS-530 Treated Fumed Silica (Cabot Corporation, Sep. 2008).
Cabot Corporation, CAB-O-SIL TS-720 Treated Fumed Silica (Cabot Corporation, Sep. 2008).
Degussa, Aerosil R 972 Hydrophobic Fumed Silica Product Information (Degussa AG, May 2005).
Evonik Industries, Aerosil R 972 Pharma Hydrophobic Colloidal Anhydrous Silica (Evonik Degussa GmbH, Feb. 2007).
Iler, "Colloidal Silica," In *The Colloid Chemistry of Silica and Silicates*, Chapter V, pp. 87, 96-98 (Cornell University Press, London, 1955).
Julien et al., "Dry Toner Technology," in *Handbook of Imaging Materials*, $2^{nd}$ Edition (Diamond et al., eds.), Chapter 5, pp. 173-204 (Marcel Dekker, Inc., New York, 2002).
Zumdahl, "Colloids" in *Chemistry, $5^{th}$ Edition* (Stratton et al., eds), Chapter 11.8, pp. 548-550 (Houghton Mifflin Company, Boston, MA, 2000).
Ochiai, Mitsuru, "Finely Dispersed Anhydrous Silica" in *Illustrated Powder Properties, 3rd edition*, Jyun-ichiro Tsubaki (editor), NGT Corporation, Tachikawa, Tokyo, Japan (publisher), p. 549 (Jun. 30, 2004).
Nissan Chemical Industries, Ltd., "Snowtex-O" Information Leaflet (2006) [as printed from http://db.nissanchem.co.jp/db/details.php?id=111 on Nov. 1, 2011].
Patent Office of the People'S Republic of China, Office Action in Chinese Patent Application No. 200880105851.5 (May 3, 2012).
Japanese Patent Office; Office Action in Japanese Patent Application No. 2009-528305 (Oct. 16, 2012).

* cited by examiner

SURFACE-TREATED METAL OXIDE PARTICLES

CROSS-REFERENCE TO RELATED APPLICATIONS

This patent application claims the benefit of U.S. Provisional Patent Application No. 60/844,828, filed Sep. 15, 2006, which is incorporated by reference.

BACKGROUND OF THE INVENTION

Hydrophobic metal oxide particles possess physical properties that are useful in a number of applications requiring a high degree of dispersibility. Some hydrophobic metal oxide particles have physical properties that are desirable for use in toner compositions.

Untreated metal oxide particles are hydrophilic due to the presence of polar groups, such as hydroxyl groups (—OH), on the surface of the untreated silica particles. By treating hydrophilic metal oxide particles, the hydrophilic nature of the particles can be reduced, thereby imparting varying degrees of hydrophobicity to the particles. Many different methods are known for treating the surface of metal oxide particles. However, the direct treatment of an aqueous dispersion of metal oxide particles is often inefficient or difficult to achieve.

Thus, there remains a desire for additional treated metal oxide particles, especially those that are useful for modifying the charge of toner particles, and for additional methods of preparing such hydrophobic metal oxide particles, especially methods that can be used to prepare hydrophobic metal oxide particles directly from an aqueous dispersion. However, not all such particles afford the charge-controlling characteristics that are required for some applications.

BRIEF SUMMARY OF THE INVENTION

The invention provides a particle composition comprising metal oxide particles surface-treated with at least one alkoxysilane compound, which metal oxide particles are hydrophobic, non-aggregated, and have a tap density of about 110 g/l to about 420 g/l, and a BET surface area of less than about 200 m$^2$/g.

The invention also provides a toner composition comprising toner particles and metal oxide particles surface-treated with at least one alkoxysilane compound, which metal oxide particles are hydrophobic, non-aggregated, and have a tap density of about 110 g/l to about 420 g/l and a BET surface area of less than about 200 m$^2$/g.

The invention further provides a method of preparing hydrophobic metal oxide particles comprising (a) providing an aqueous dispersion of hydrophilic metal oxide particles, (b) combining the dispersion with at least one alkoxysilane treating agent to provide a reaction mixture, wherein the reaction mixture is basic, and (c) drying the reaction mixture to provide hydrophobic metal oxide particles having a tap density of about 110 g/l to about 420 g/l and a BET surface area of less than about 200 m$^2$/g.

The invention additionally provides a method of preparing hydrophobic metal oxide particles comprising (a) providing an aqueous dispersion of non-aggregated hydrophilic metal oxide particles, (b) combining the dispersion with at least one alkoxysilane treating agent to provide a reaction mixture, wherein the reaction mixture is basic, (c) drying the reaction mixture to provide hydrophobic metal oxide particles, and (d) reducing the agglomerate size of the hydrophobic metal oxide particles by jet milling or hammer milling.

BRIEF DESCRIPTION OF THE SEVERAL VIEWS OF THE DRAWING(S)

DETAILED DESCRIPTION OF THE INVENTION

Figure 1:
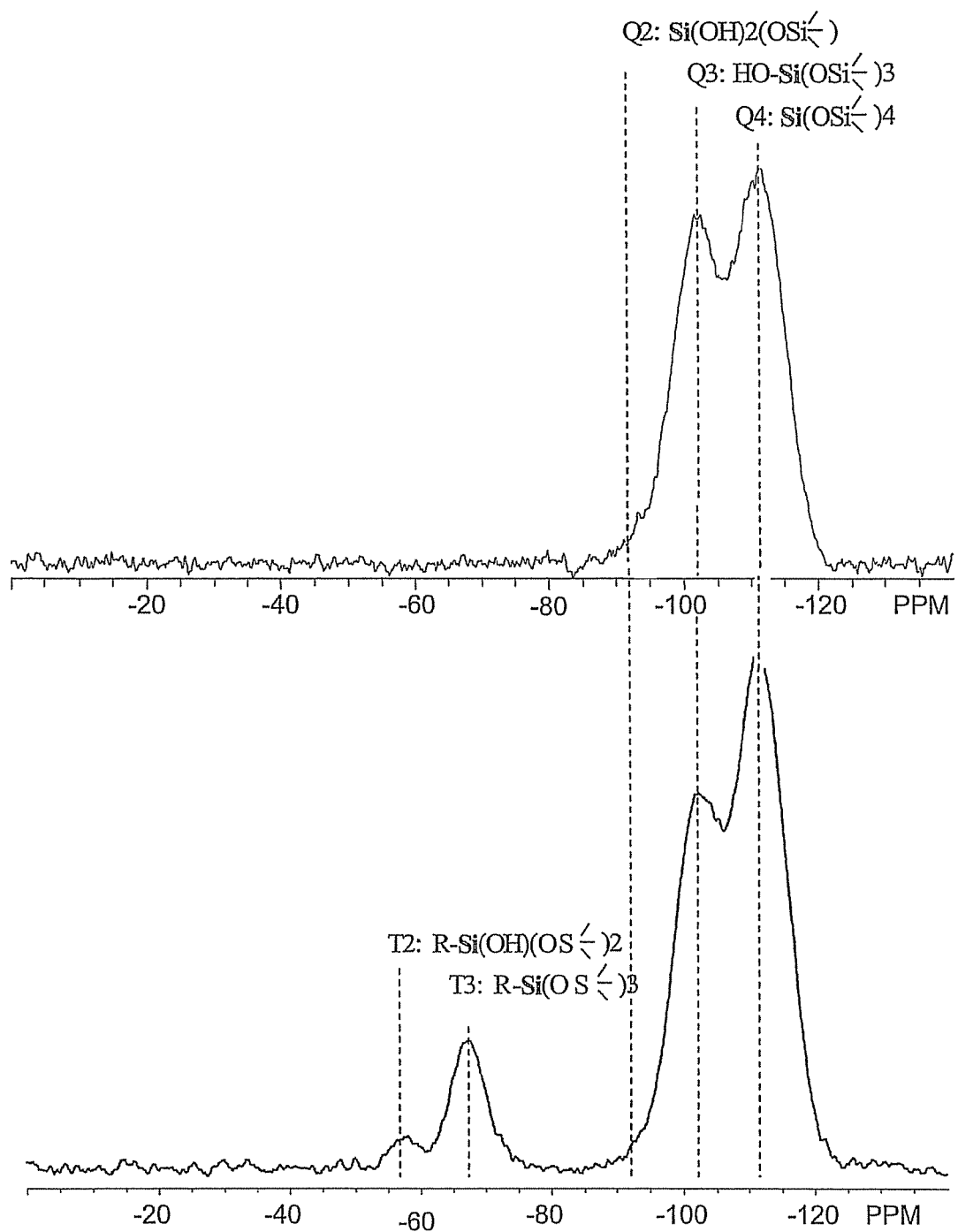
FIG. 1 depicts the NMR spectra of untreated silica particles and silica particles treated with OTES (octyltriethoxysilane).

The invention provides a particle composition comprising metal oxide particles surface-treated with at least one alkoxysilane compound, which metal oxide particles are hydrophobic, non-aggregated, and have a tap density of about 110 g/l to about 420 g/l, and a BET surface area of less than about 200 m$^2$/g. The inventive particles can be utilized in compositions containing toner particles. The method of preparing the inventive metal oxide particles comprises (a) providing an aqueous dispersion of hydrophilic metal oxide particles, (b) combining the dispersion with at least one alkoxysilane treating agent to provide a reaction mixture, wherein the reaction mixture is basic, and (c) drying the reaction mixture to provide hydrophobic metal oxide particles. The resulting hydrophobic metal oxide particles can have a tap density of about 110 g/l to about 420 g/l and a BET surface area of less than about 200 m$^2$/g and/or the method can further comprise an additional step wherein the average particle size of the hydrophobic metal oxide particles is reduced.

"Hydrophobic" metal oxide particles, as the term is used herein, encompasses varying levels or degrees of hydrophobicity. The degree of hydrophobicity imparted to the metal oxide particles will vary depending upon the type and amount of treating agent used. Hydrophobic metal oxide particles according to the invention preferably, but not necessarily, have about 25% or more (e.g., about 35% or more, about 45% or more, or about 50% or more) of the available metal oxide surface hydroxyl groups reacted. Generally, the hydrophobic metal oxide particles according to the invention have about 85% or less (e.g., about 75% or less, or about 65% or less) of the available metal oxide surface hydroxyl groups reacted.

The metal oxide particle can comprise any suitable type of metal oxide particle, such as silica, alumina, ceria, or titania. Preferably, the metal oxide particle is a colloidal metal oxide particle, such as a colloidal silica particle. Colloidal metal oxide particles are non-aggregated, individually discrete particles, which typically are spherical or nearly spherical in shape, but can have other shapes (e.g., shapes with generally elliptical, square, or rectangular cross-sections). Such particles are structurally different from fumed or pyrogenically prepared particles, which are chain-like structures of aggregated primary particles.

Non-aggregated metal oxides (e.g., colloidal metal oxides), which can be treated to provide a surface treated metal oxide in accordance with the invention, are commercially available, or can be prepared by known methods from various starting materials (e.g., wet-process type metal oxides). Silica particles can be prepared, for example, from silicic acid derived from an alkali silicate solution having a pH of about 9 to about 11, wherein the silicate anions undergo polymerization to produce discrete silica particles having the desired average particle size in the form of an aqueous dispersion. Typically, the colloidal metal oxide starting material will be available as a sol, which is a dispersion of colloidal metal oxide in a suitable solvent, most often water alone or with a co-solvent and/or stabilizing agent. See, e.g., Akitoshi Yoshida, *Silica Nucleation, Polymerization, and Growth Preparation of Monodispersed Sols*, in Colloidal Silica Fundamentals and Applications 47-56 (H. E. Bergna & W. O. Roberts, eds., 2006). Non-limiting examples of commercially available colloidal silica suitable for use in the invention include SNOWTEX® products from Nissan Chemical, Nex-Sil™ and NexSil A™ series products available from Nyacol Nanotechnologies, Inc., and Levasil® products available from H. C. Starck.

The colloidal silica from which the treated metal oxide particle can be prepared often contains alkali metal cations as a result of the method by which such colloidal silica was manufactured or stabilized in dispersion. The alkali metal cations may be present both in the interior portions of the particles, as well as on the surface of the particles. "Free alkali metal cation" refers to an alkali metal cation that is solubilized in the aqueous phase of a dispersion of colloidal silica, or that is present at the surface of the metal oxide particle, and does not refer to alkali metal cation that may be bound or trapped within the interior of the metal oxide particles and thus inaccessible to the aqueous phase. The alkali metal cation can be sodium, potassium, or any other Group I metal cation.

The free alkali metal cation content of the metal oxide dispersion of silica can be reduced, for example, by treatment of the aqueous colloidal dispersion with an acidic ion exchange resin. Alternatively, or in addition, the free alkali metal cation content of the base-stabilized dispersion of silica can be reduced by using ultrafiltration, e.g., difiltration. Reduction of the free alkali metal cation content also may reduce the pH of the dispersion. If desired, the pH can be adjusted without increasing the alkali metal content by addition of an amine or ammonium hydroxide ($NH_4OH$). In this respect, it is also possible to avoid the need to reduce the alkali metal cation content of the dispersion, in accordance with this preferred aspect of the invention, by using an ammonium-stabilized aqueous dispersion of metal oxide as a starting material.

Reduction of the free alkali metal cation content of the aqueous dispersion of metal oxide, to the extent it is required, can be performed at any time before or after the at least one alkoxysilane is added to the aqueous dispersion of metal oxide. For example, the free alkali metal cation reducing treatment (e.g, ion exchange, ultrafiltration, or the like) can be performed as part of the production process of the metal oxide dispersion, or can be performed on a commercially available aqueous dispersion of metal oxide before use in the invention (e.g., about 1 hour or less before use, or about 1 day or less before use, or about 1 week or less before use). Alternatively, such treatment can be employed after the at least one alkoxysilane is combined with the dispersion of metal oxide particles. Instead, or in addition, free alkali metal cation reducing treatment also can be used to reduce the alkali metal content of the treated metal oxide particles at a later time, for example, by dispersing dried, treated metal oxide particles in water or an acceptable solvent and reducing the alkali metal content of the dispersion, after which the treated metal oxide particles can be isolated and/or dried by any suitable method.

An ion-exchanged aqueous dispersion is typically characterized by having a pH of about 1 to about 7 and having a content of free alkali metal cation of about 0.05 wt. % or less. The basic aqueous dispersion is typically characterized by having a pH of about 7 to about 12. Such a dispersion can be used to prepare the inventive particles, provided that the pH of the reaction mixture is adjusted to a pH of about 7 or more.

The hydrophilic metal oxide particle is treated with at least one alkoxysilane compound. The at least one alkoxysilane compound has the general formula: $R^1_x Si(OR^2)_{4-x}$ wherein $R^1$ is selected from the group consisting of $C_1$-$C_{30}$ branched and straight chain alkyl, aminoalkyl, alkenyl, and aminoalkenyl, $C_3$-$C_{10}$ cycloalkyl, and $C_6$-$C_{10}$ aryl, $R^2$ is a $C_1$-$C_{10}$ branched or straight chain alkyl, and x is an integer of 1-3. Examples of suitable alkoxylsilane compounds include but are not limited to trimethylmethoxysilane, dimethyldimethoxysilane, methyltrimethoxysilane, and the like.

Preferably, the alkoxysilane compound is a trialkoxysilane compound. The trialkoxysilane compound can be any suitable trialkoxysilane. For example, the trialkoxysilane compound can have the formula: $R^1 Si(OR^2)_3$ wherein $R^1$ is selected from the group consisting of $C_1$-$C_{30}$ branched and straight chain alkyl, aminoalkyl, alkenyl, and aminoalkenyl, and $C_3$-$C_{10}$ cycloalkyl, and $R^2$ is a $C_1$-$C_{10}$ branched or straight chain alkyl. Preferably, the trialkoxysilane compound is selected from the group consisting of methyltrimethoxysilane, ethyltrimethoxysilane, propyltrimethoxysilane, butyltrimethoxysilane, pentyltrimethoxysilane, hexyltrimethoxysilane, heptyltrimethoxysilane, octyltrimethoxysilane, nonyltrimethoxysilane, decyltrimethoxysilane, undecyltrimethoxysilane, dodecyltrimethoxysilane, tetradecyltrimethoxysilane, stearyltrimethoxysilane, methyltriethoxysilane, ethyltriethoxysilane, propyltriethoxysilane, butyltriethoxysilane, pentyltriethoxysilane, hexyltriethoxysilane, heptyltriethoxysilane, octyltriethoxysilane, nonyltriethoxysilane, decyltriethoxysilane, undecyltriethoxysilane, dodecyltriethoxysilane, tetradecyltriethoxysilane, stearyltriethoxysilane, and combinations thereof. More preferably, the trialkoxysilane compound is selected from the group consisting of hexyltrimethoxysilane, heptyltrimethoxysilane, octyltrimethoxysilane, nonyltrimethoxysilane, decyltrimethoxysilane, undecyltrimethoxysilane, dodecyltrimethoxysilane, tetradecyltrimethoxysilane, stearyltrimethoxysilane, methyltriethoxysilane, ethyltriethoxysilane, propyltriethoxysilane, butyltriethoxysilane, pentyltriethoxysilane, hexyltriethoxysilane, heptyltriethoxysilane, octyltriethoxysilane, nonyltriethoxysilane, decyltriethoxysilane, undecyltriethoxysilane, dodecyltriethoxysilane, tetradecyltriethoxysilane, stearyltriethoxysilane, 3-aminopropyltriethoxysilane, 3-aminobutyltriethoxysilane, 3-aminobutyltriethoxysilane, and combinations thereof.

The metal oxide particle can be treated with more than one alkoxysilane compound (e.g., at least two alkoxysilane compounds, or at least three alkoxysilane compounds). For example, the metal oxide particles can be treated with octyltriethoxysilane and 3-aminopropyltriethoxysilane.

The hydrophobic metal oxide particle has a pour density of less than about 300 g/l. Typically, the metal oxide particle has a pour density of about 50 g/l or more (e.g., about 60 g/l or more, about 70 g/l or more, about 80 g/l or more, about 90 g/l or more, or about 100 g/l or more). The pour density of the metal oxide particle typically will be about 280 g/l or less, more typically will be about 270 g/l or less (e.g., about 250 g/l or less, about 240 g/l or less, about 230 g/l or less, about 220 g/l or less, or about 210 g/l or less). Preferably, the pour density of the metal oxide particle is about 20 g/l to about 300 g/l, and more preferably about 30 g/l to about 300 g/l (e.g., about 50 g/l to about 300 g/l, about 75 g/l to about 300 g/l, about 80 g/l to about 280 g/l, about 100 g/l to about 300 g/l, or about 100 g/l to about 280 g/l).

Typically, the metal oxide particle has a tap density of about 75 g/l or more, or about 100 g/l or more. The tap density of the metal oxide particle typically will be about 450 g/l or less, more typically will be about 420 g/l or less (e.g., about 400 g/l or less, about 380 g/l or less, about 350 g/l or less, about 320 g/l or less, about 300 g/l or less, about 280 g/l or less, about 250 g/l or less, about 230 g/l or less, about 210 g/l or less, or about 180 g/l or less). Preferably, the tap density of the metal oxide particle is about 50 g/l to about 420 g/l, about 75 g/l to about 400 g/l, about 80 g/l to about 380 g/l, about 110 g/l to about 420 g/l, or about 150 g/l to about 400 g/l. The tap density of the metal oxide particle can be determined using a tap volumeter and the following equation: tap density (g/l)= (weight of the treated metal oxide particles in grams)×(1000/(volume of the treated metal oxide particles in ml)). The ratio of pour to tap density is approximately 0.7. Any suitable number of taps can be taken by the tap volumeter. Preferably, the tap volumeter takes about 300 taps or more (e.g., about 600 taps or more, about 1250 taps or more, or 3000 taps or more) of the sample of treated metal oxide particles. All tap densities described herein, unless otherwise indicated, were measured after 3000 taps were taken.

The hydrophobic metal oxide particle has a BET surface area of less than about 200 m$^2$/g (determined by the method of S. Brunauer, P. H. Emmet, and I. Teller, *J. Am. Chemical Society*, 60, 309 (1938), which is commonly referred to as the BET method). Typically, the metal oxide particle has a BET surface area of about 10 m$^2$/g or more (e.g., about 20 m$^2$/g or more, about 30 m$^2$/g or more, about 40 m$^2$/g or more, about 50 m$^2$/g or more, or about 60 m$^2$/g or more). The BET surface area of the metal oxide particle typically will be about 180 m$^2$/g or less, more typically will be about 160 m$^2$/g or less (e.g., about 140 m$^2$/g or less, about 120 m$^2$/g or less, about 100 m$^2$/g or less, about 80 m$^2$/g or less, about 70 m$^2$/g or less, or about 50 m$^2$/g or less). Preferably, the BET surface area of the metal oxide particles is about 10 m$^2$/g to about 200 m$^2$/g, and more preferably about 20 m$^2$/g to about 180 m$^2$/g (e.g., about 20 m$^2$/g to about 160 m$^2$/g, about 20 m$^2$/g to about 140 m$^2$/g, about 20 m$^2$/g to about 130 m$^2$/g, about 20 m$^2$/g to about 120 m$^2$/g, or about 20 m$^2$/g to about 100 m$^2$/g).

The treated metal oxide particles can have any suitable average non-agglomerated particle size. The particle size refers to the diameter of the smallest sphere that encloses the non-agglomerated particle. Agglomerated particles (agglomerates) are composed of several primary particles loosely attached to each other, usually by van der Waals forces. This is in contrast to aggregated particles (aggregates), in which the bonds between primary particles are stronger, as is the case when the particles sinter. As a result, de-agglomeration can be easily achieved for agglomerates. For example, dispersion of treated metal oxide particles with toner particles (dry dispersion) or in a suitable liquid (e.g., tetrahydrofuran (THF)) using high speed agitation or sonication can be used to reverse agglomeration. However, it is considerably more difficult or even impossible to reverse aggregation to any significant extent. The average particle size of the non-agglomerated hydrophobic metal oxide particles can be, for example, less than about 1 micron (e.g., about 0.8 microns or less, about 0.7 microns or less, about 0.5 microns or less, or about 0.3 microns or less). The average particle size of the non-agglomerated hydrophobic metal oxide particles can be about 0.01 microns or more (e.g., about 0.05 microns or more, about 0.1 microns or more, about 0.2 microns or more, or about 0.3 microns or more). Thus, the average particle size of the non-agglomerated hydrophobic metal oxide particles can be, for example, from about 0.01 microns to about 5 microns (e.g., from about 0.05 microns to about 3 microns, from about 0.1 microns to about 1 micron, from about 0.2 microns to about 0.8 microns, or from about 0.3 microns to about 0.6 microns).

The hydrophilic metal oxide particle can have any suitable true density. Typically, the metal oxide particle has a true density of about 1.5 g/cm$^3$ or more (e.g., about 1.6 g/cm$^3$ or more, about 1.7 g/cm$^3$ or more, about 1.8 g/cm$^3$ or more, about 1.9 g/cm$^3$ or more, or about 2 g/cm$^3$ or more). The true density of the metal oxide particle typically will be about 5 g/cm$^3$ or less, more typically will be about 4 g/cm$^3$ or less (e.g., about 3.5 g/cm$^3$ or less, about 3 g/cm$^3$ or less, about 2.8 g/cm$^3$ or less, or about 2.5 g/cm$^3$ or less). Preferably, the true density of the metal oxide particle is about 0.1 g/cm$^3$ to about 5 g/cm$^3$, and more preferably about 0.5 g/cm$^3$ to about 4 g/cm$^3$ (e.g., about 1 g/cm$^3$ to about 3.5 g/cm$^3$, about 1.5 g/cm$^3$ to about 3 g/cm$^3$, about 1.8 g/cm$^3$ to about 2.8 g/cm$^3$, about 2 g/cm$^3$ to about 2.5 g/cm$^3$, or about 2.2 g/cm$^3$ to about 2.4 g/cm$^3$).

The surface treatment of a hydrophilic metal oxide particle with an alkoxysilane generates various patterns of substituted silicon atoms attached to the surface of the metal oxide particle or attached indirectly to the surface of the metal oxide particle. These substitution patterns have been referred to in the literature as M sites, D sites, and T sites. See, for example, Sindorf, Dean William, "Silicon-29 and Carbon-13 CP/MAS NMR Studies of Silica Gel and Bonded Silane Phases," Department of Chemistry, Colorado State University, Fort Collins, Colo., 1982. The correlation of the M sites, D sites, and T sites to the resonance signals in the CP/MAS $^{29}$Si NMR spectrum also is discussed in Maciel, G., Sindorf, D. W., *J. Am. Chem. Soc.*, 102: 7607-7608 (1980), Sindorf, D. W., Maciel, G., *J. Phys. Chem.*, 86: 5208-5219 (1982), and Sindorf, D. W., Maciel, G., *J. Am. Chem. Soc.*, 105: 3767-3776 (1983).

In particular, the surface treatment of a hydrophilic metal oxide particle with at least one trialkoxysilane compound in accordance with one embodiment of the invention provides metal oxide particles having predominantly substitution patterns referred to as T2 and T3 sites. As used herein, T2 sites correspond to a silicon atom originating from the alkoxysilane compound having two bonds to oxygen atoms further bonded to silicon atoms, at least one of which is on the metal oxide particle surface, one bond to an oxygen atom comprising a silanol (Si—OH) group, and one bond to a carbon atom. T2 sites are represented by formula (I): R—Si(OH)—(OSi—P$^1$)(OSiP$^2$) wherein the group R is as defined herein for the alkoxysilane compound, and P$^1$ and P$^2$ independently represent a bond to a silicon atom on a particle surface and/or a silicon atom of another silane-containing molecule. Si atoms corresponding to T2 sites have been correlated with the resonance signals with chemical shifts in the range from −56 ppm to −59 ppm in the CP/MAS $^{29}$Si NMR spectrum, wherein the chemical shift in ppm is measured relative to the standard tetramethylsilane.

As used herein, T3 sites correspond to a silicon atom originating from the alkoxysilane compound having three bonds to an oxygen atom further bonded to silicon atoms. At least one of the silicon atoms is a silicon atom on a particle. The sites are represented by the formula (II): R—Si(OSi—P$^1$)(OSi—P$^2$)(OSi—P$^3$) wherein the group R is as herein defined for the alkoxysilane compound and wherein P$^1$, P$^2$, and P$^3$ independently represent a bond to a silicon atom on a particle surface and/or a silicon atom of another silane-containing molecule. Si atoms corresponding to T3 sites have been correlated with the resonance signals with chemical shifts in the range from −65 ppm to −69 ppm in the CP/MAS $^{29}$Si NMR spectrum, wherein the chemical shift in ppm is measured relative to the standard tetramethylsilane.

As defined herein, T2 is the integrated intensity of a peak having a chemical shift in the CP/MAS $^{29}$Si NMR spectrum centered within the range of −56 ppm to −59 ppm. T3 is the integrated intensity of a peak having a chemical shift in the CP/MAS $^{29}$Si NMR spectrum centered within the range of −65 ppm to −69 ppm. The intensity of a peak refers to the maximum peak height of the signal at that approximate location or the area of the peak occurring within the recited ranges, as calculated using standard calculation methods well known to those skilled in the art.

The hydrophobic metal oxide particles preferably have a ratio of T3 to T2 (i.e., T3:T2), based on the integrated area of the peaks, of about 1.5 or more (e.g., about 2 or more, about 2.5 or more, about 3 or more, or about 3.5 or more), wherein T2 and T3 are as defined herein.

The hydrophobic metal oxide particles can be formulated as a dry particle composition (e.g., a dry powder) or as a wet particle composition (e.g., dispersion) comprising the hydrophobic metal oxide particles. The dispersion can comprise any suitable dispersant, preferably water alone or with a co-solvent, treating agents, or additives of any type commonly used in dispersions of hydrophobic metal oxide particles.

The hydrophobic metal oxide particles can be used for many different applications including but not limited to toner compositions, antiblocking agents, adhesion modifiers, polymer additives (e.g., for elastomers and rubbers, such as silicone rubbers), abrasion-resistant coatings and films, delustering coatings and films, reological control agents (e.g., for epoxies or liquid polymers), and mechanical/optical control agents (e.g., for composites and plastics). The hydrophobic metal oxide particles are especially useful in toner compositions. In that regard, the invention provides a toner composition comprising toner particles and metal oxide particles surface-treated with at least one alkoxysilane compound, which metal oxide particles are hydrophobic, non-aggregated, and have a tap density of about 110 g/l to about 420 g/l or less and a BET surface area of about 200 m$^2$/g or less.

All aspects of the hydrophobic metal oxide particles used in the toner composition are as described with respect to the particle composition of the invention.

The tribocharge of toner compositions containing the treated metal oxide particles can be either positive or negative. The tribocharge of a toner composition containing the inventive treated metal oxide particles is affected by the presence of the treated particles. Without wishing to be bound by a particular theory, it is thought that the presence of the treated metal oxide particles stabilizes and increases the positive or negative tribocharge of toner compositions containing the metal oxide particles.

Toner compositions containing the treated metal oxide particles can be formulated, for example, by mixing 4 wt. % of the treated particles in a laboratory blender with pulverized styrene acrylate toner particles free of any external additives and having an average diameter of 9 μm. Toner compositions containing the treated particles can be developed, for example, by rolling for 30 minutes at a 2/98 wt. % toner/carrier ratio in glass jars. The carrier can be 70 μm Cu—Zn ferrite coated with silicone resin. Samples can be conditioned in a standard humidity chamber at either a high humidity and high temperature (30° C. and 80% relative humidity) or at a low humidity and low temperature (18° C. and 15% relative humidity) overnight.

The tribocharge of toner compositions containing the treated metal oxide particles can be either positive or negative. Tribocharge measurements can be made using suitable techniques and equipment known in the art (e.g., Vertex T-150 tribocharger). Measurements can be made after conditioning the toner particles overnight in a standard humidity chamber at 30° C. and 80% relative humidity (HH) and at 18° C. and 15% relative humidity (LL). The toner particles (e.g., of a toner composition comprising about 4 wt. % treated metal oxide particles) preferably have a tribocharge at HH conditions of about −40 μC/g to about +15 μC/g (e.g., about −40 μC/g to about −20 μC/g, about −40 μC/g to about 0 μC/g, about −5 μC/g to about +10 μC/g, about 0 μC/g to about +5 μC/g, or about +5 μC/g to about +10 μC/g). The toner particles preferably have a tribocharge at LL conditions of about −100 μC/g to about +25 μC/g (e.g., about −80 μC/g to about −50 μC/g, about −80 μC/g to about 0 μC/g, about −5 μC/g to about +10 μC/g, about +5 μC/g to about +35 μC/g, or about +10 μC/g to about +25 μC/g).

The free flow of a toner composition containing the inventive treated metal oxide particles is affected by the presence of the treated particles. Without wishing to be bound by a particular theory, it is thought that the presence of the treated metal oxide particles, especially particles which have been jet milled, improves the free flow of toner compositions containing the metal oxide particles due to the lower tap and pour densities of the treated particles. In the context of the invention, free flow is the percentage of toner discharged from a grounded metal role tube of 25 mm diameter and 350 mm in length, with seven 0.5 mm discharge holes, that contains 40 g of the toner composition and is rotated at 30 rpm for one minute for a total of 30 rotations. The toner composition can have a free flow of about 0.5 wt. % loss or more (e.g., about 1 wt. % loss or more, about 1.5 wt. % loss or more, about 2 wt. % loss or more, or about 3.5 wt. % loss or more). The free flow of the toner composition typically will be about 8 wt. % loss or less (e.g., about 6 wt. % loss or less, about 5 wt. % loss or less, about 4 wt. % loss or less, or about 3 wt. % loss or less). Preferably, the free flow of the toner composition is about 0.5 wt. % loss to about 8 wt. % loss (e.g., about 1 wt. % loss to about 6 wt. % loss, about 1.5 wt. % loss to about 5 wt. % loss, or about 2 wt. % loss to about 4.5 wt. % loss).

The hydroplilic metal oxide particles that are treated with the alkoxysilane compound are in an aqueous dispersion. The aqueous dispersion of metal oxide particles preferably is colloidally stable. The colloidal stability of the dispersion prevents any substantial portion of the particles fiom irreversibly agglomerating or gelling, or from settling out of the dispersion during use. The aqueous dispersion of metal oxide particles used in conjunction with the invention preferably has a degree of colloidal stability such that the average overall particle size of the silica in dispersion, as measured by dynamic light scattering, does not change over a period of 1 hour or more (e.g., about 8 hours or more, or about 24 weeks or more), more preferably 2 weeks or more (e.g., about 4 weeks or more, or about 6 weeks or more), most preferably 8 weeks or more (e.g., about 10 weeks or more, or about 12 weeks or more), or even about even 16 weeks or more.

The invention provides a method of preparing hydrophobic metal oxide particles comprising (a) providing an aqueous dispersion of hydrophilic metal oxide particles, (b) combining the dispersion with at least one alkoxysilane treating agent to provide a reaction mixture, wherein the reaction mixture is basic, and (c) drying the reaction mixture to provide hydrophobic metal oxide particles. According to one aspect of the invention, the hydrophobic metal oxide particles have a tap density of about 110 g/l to about 420 g/l and a BET surface area of less than about 200 m$^2$/g. According to another aspect of the invention, the agglomerate size of the hydrophobic metal oxide particles can be reduced by jet milling or hammer milling.

The aqueous dispersion containing the hydrophilic metal oxide particles can be a commercially available metal oxide dispersion, as described herein. Alternatively, the aqueous dispersion can be prepared by any suitable technique. In one embodiment, the metal oxide particles can be prepared via a wet process, such as by mixing a metal oxide with water and a water-soluble organic solvent. The water-soluble organic solvent can be any suitable water-soluble organic solvent, such as an alcohol (e.g., methanol, ethanol, n-propanol, 2-propanol, n-butanol, isobutanol, sec-butanol, tert-butanol, n-propanol, ethylene glycol, and propylene glycol), ketone (e.g., acetone and 2-butanone), ether (e.g., tetrahydrofuran and 1,2-dimethoxyethane), and combinations thereof. The water and water-soluble organic solvent can be added in any order. For example, the water can be added before the water-soluble organic solvent, or vice versa. Although not wishing to be bound by a particular theory, it is thought that adding the water before the water-soluble organic solvent prevents the dispersion from gelling. Typically, the reaction mixture will comprise no more than about 50 wt. % of organic solvent, and preferably will comprise not more than about 40 wt. % of organic solvent.

The water-soluble organic solvent to water volume ratio can be any suitable ratio. The ratio typically is less than about 10 (e.g., about 8 or less, about 6 or less, about 5 or less, about 3 or less, or about 2 or less). The ratio can be about 0.05 or more (e.g., about 0.1 or more, about 0.5 or more, about 0.7 or more, about 1 or more, or about 1.2 or more). The ratio can be, for example, from about 0.05 to about 10 (e.g., from about 0.1 to about 5, or from about 0.2 to about 2).

The aqueous dispersion containing the hydrophilic metal oxide particles can contain any suitable amount of metal oxide particles. The aqueous dispersion typically comprises about 30 wt. % or less (e.g., about 25 wt. % or less, about 20 wt. % or less, about 15 wt. % or less, about 10 wt. % or less, or about 5 wt. % or less) metal oxide particles. The aqueous dispersion can comprise about 5 wt. % or more (e.g., about 10 wt. % or more, about 15 wt. % or more, about 20 wt. % or more, about 25 wt. % or more, or about 30 wt. % or more) metal oxide particles. Thus, the aqueous dispersion can comprise, for example, from about 5 wt. % to about 30 wt. % (e.g., from about 10 wt. % to about 25 wt. %, or from about 15 wt. % to about 20 wt. %) metal oxide particles.

The aqueous dispersion containing the hydrophilic metal oxide particles can be combined with at least one alkoxysilane treating agent to provide a reaction mixture in any suitable manner. The dispersion can be acidic or basic, and the pH of the dispersion can be altered by the addition of the at least one alkoxysilane treating agent.

The amount of the at least one alkoxysilane compound that is added to the aqueous dispersion containing the hydrophilic metal oxide particles can be any suitable amount. The amount of the at least one alkoxysilane compound typically comprises less than about 50 µmole/m$^2$ metal oxide particles (e.g., about 25 µmole/m$^2$ metal oxide particles or less, about 15 µmole/m$^2$ metal oxide particles or less, about 10 µmole/m$^2$ metal oxide particles or less, or about 5 µmole/m$^2$ metal oxide particles or less). The amount of the at least one alkoxysilane compound can comprise about 0.1 µmole/m$^2$ metal oxide particles or more (e.g., about 0.5 µmole/m$^2$ metal oxide particles or more, about 1 µmole/m$^2$ metal oxide particles or more, or about 2 µmole/m$^2$ metal oxide particles or more). Thus, the amount of the at least one alkoxysilane compound can comprise, for example, from about 0.1 µmole/m$^2$ metal oxide particles to about 50 µmole/m$^2$ metal oxide particles (e.g., from about 0.5 µmole/m$^2$ metal oxide particles to about 25 µmole/m$^2$ metal oxide particles, or from about 2 µmole/m$^2$ metal oxide particles to about 15 µmole/m$^2$ metal oxide particles).

The pH of the aqueous dispersion can be any suitable pH before the at least one alkoxysilane is added to the dispersion. Regardless of whether the starting dispersion is acidic, basic, or neutral, the reaction mixture should have a basic pH, i.e., a pH of about 7 or more. The pH of the reaction mixture can be, for example, about 7 or more (e.g., about 8 or more, about 9 or more, about 10 or more, about 11 or more, or about 12 or more). Generally, the pH of the reaction mixture will be from about 7 to about 12 (e.g., from about 8 to about 11, from about 9 to about 10.5, or from about 9.5 to about 10.5).

The reaction between the aqueous dispersion containing the metal oxide particles and the alkoxysilane compound can occur at any suitable temperature and for any suitable amount of time that allows the alkoxysilane compound to react completely, or to any extent desired, with the aqueous dispersion of metal oxide particles. Generally, the reaction mixture is maintained at a temperature of about 20° C. to about 100° C. (e.g., about 30° C. to about 70° C., or about 45° C. to about 75° C.) for about 5 minutes or longer (e.g., about 30 minutes or longer, about 1 hour or longer), or even about 2 hours or longer (e.g., about 3 hours or longer, or about 4 hours or longer). Longer reaction times (e.g., 5 hours or more, 10 hours or more, or even 20 hours or more) may be required depending on the particular reaction conditions (e.g., temperature and concentration of reagents).

Additional alkoxysilanes, silazanes, or other treating agents can be added (e.g., a second, third, or fourth alkoxysilane, silazane, or treating agent) at any suitable time before or after the addition of the first alkoxysilane compound. After the addition of another treating agent, the temperature of the reaction mixture can be adjusted to any suitable temperature for any suitable amount of time that allows the additional alkoxysilane compound to react completely, or to any extent desired, with the aqueous dispersion of metal oxide particles.

Preferably, the reaction mixture containing the hydrophobic metal oxide particles is dried to form a powder. The drying of the reaction mixture can be effected in any suitable manner. For example, spray drying can be used to dry the hydrophobic metal oxide particles. Spray drying involves spraying the reaction mixture, or some portion thereof, comprising the hydrophobic metal oxide particles as a fine mist into a drying chamber, wherein the fine mist is contacted with hot air causing the evaporation of volatile components of the reaction mixture. The temperature chosen for the hot air will depend, at least in part, on the specific components of the reaction mixture that require evaporation. Typically, the drying temperature will be about 40° C. or higher (e.g., about 50° C. or higher) such as about 70° C. or higher (e.g., about 80° C. or higher) or even about 120° C. or higher (e.g., about 130° C. or higher). Thus, the drying temperatures generally can be within the range of about 40-250° C. (e.g., about 50-200° C.), such as about 60-200° C. (e.g., about 70-175° C.), or about 80-150° C. (e.g., about 90-130° C.).

The hydrophobic metal oxide particles can be isolated from the reaction mixture prior to drying, or the hydrophobic metal oxide particles can be dried directly from the reaction mixture. Any suitable method can be used to isolate the hydrophobic metal oxide particles from the reaction mixture. Suitable methods include filtration and centrifugation.

The hydrophobic metal oxide particles can be dried after isolation from the reaction mixture, or directly from the reaction mixture, by any suitable technique, e.g., by evaporating the volatile components of the reaction mixture from the hydrophobic metal oxide particles. Evaporation of the volatile components of the reaction mixture can be accomplished using any suitable techniques, e.g., heat and/or reduced atmospheric pressure. When heat is used, the hydrophobic metal oxide particles can be heated to any suitable drying temperature, for example, by using an oven or other similar device. The temperature can be as recited for the spray drying embodiment of the invention.

The hydrophobic metal oxide particles can be dried at any pressure that will provide a useful rate of evaporation. When drying temperatures of about 120° C. and higher (e.g., about 120-150° C.) are used, drying pressures of about 125 kPa or less (e.g., about 75-125 kPa) are desirable. At drying temperatures lower than about 120° C. (e.g., about 40-120° C.), drying pressures of about 100 kPa or less (e.g., about 75 kPa or less) are desirable. Of course, reduced pressure (e.g., pressures of about 100 kPa or less, 75 kPa or less, or even 50 kPa or less) can be used as a sole method for evaporating the volatile components of the reaction mixture.

Alternatively, the hydrophobic metal oxide particles can be dried by lyophilization, wherein the liquid components of the reaction mixture are converted to a solid phase (i.e., frozen) and then to a gas phase by the application of a vacuum. For example, the reaction mixture comprising the hydrophobic metal oxide particles can be brought to a suitable temperature (e.g., about −20° C. or less, or about −10° C. or less, or even −5° C. or less) to freeze the liquid components of the reaction mixture, and a vacuum can be applied to evaporate those components of the reaction mixture to provide dry hydrophobic metal oxide particles.

The hydrophobic metal oxide particles can be washed prior to or after isolation and/or drying from the reaction mixture. Washing the hydrophobic metal oxide particles can be performed using a suitable washing solvent, such as water, a water-miscible organic solvent, a water-immiscible solvent, or a mixture thereof. The washing solvent can be added to the reaction mixture and the resulting mixture suitably mixed, followed by filtration, centrifugation, or drying to isolate the washed hydrophobic metal oxide particles. Alternatively, the hydrophobic metal oxide particles can be isolated from the reaction mixture prior to washing. The washed hydrophobic metal oxide particles can be further washed with additional washing steps followed by additional filtration, centrifugation, and/or drying steps.

The hydrophobic metal oxide particles have an overall particle size that is dependent, at least in part, on the overall particle size of the metal oxide particles in the initial dispersion. The average overall particle size of the hydrophobic metal oxide particles can be determined by any suitable method, many of which methods are known in the art, such as dynamic light scattering. Preferred average particle sizes of the hydrophobic metal oxide particles prepared in accordance with the method of the invention are as described with respect to the treated metal oxide particles of the invention. Desirably, the average particle size of the hydrophobic, non-aggregated particle prepared in accordance with the method of the invention is within about 50%, preferably within about 30% (e.g., within about 20%, about 15%, about 10%, or even about 5%) of the average particle size of the metal oxide particle of the starting dispersion. Preferably, the average particle size of the hydrophobic metal oxide particles is further reduced after drying. The agglomerate size of the hydrophobic metal oxide particles is also preferably reduced after drying. Suitable processes for the reduction of the particle size and agglomerate size of the hydrophobic metal oxide particles include but are not limited to wet or dry grinding, hammer milling, and jet milling.

The carbon content of the hydrophobic metal oxide particles can be used as an indicator of the level of treatment of the hydrophobic metal oxide particles and, thus, as an indicator of the degree of hydrophobicity. The carbon content of the treated particles can be determined using commercially available carbon analyzers (e.g., Leco C-200). The hydrophobic metal oxide particles prepared in accordance with the invention desirably have a carbon content of about 0.1 wt. % or more (e.g., about 0.2 wt. % or more, about 0.3 wt. % or more, about 0.4 wt. % or more, about 0.5 wt. % or more, or about 0.8 wt. % or more). The carbon content of the treated metal oxide particles typically comprises less than about 10 wt. % (e.g., about 8 wt. % or less, about 7 wt. % or less, about 6 wt. % or less, or about 5 wt. % or less). Thus, the carbon content of the treated metal oxide particles can be, for example, from about 0.01 wt. % to about 10 wt. % (e.g., from about 0.05 wt. % to about 8 wt. %, from about 0.1 wt. % to about 7 wt. %, from about 0.3 wt. % to about 7 wt. %, or from about 0.5 wt. % to about 6 wt. %).

The following examples further illustrate the invention but, of course, should not be construed as in any way limiting its scope.

EXAMPLE 1

This example illustrates the preparation of hydrophobic metal oxide particles by treating colloidal silica particles with an alkoxysilane compound.

The reactor was charged with 41.6 kg of 40 wt. % colloidal silica in an aqueous solution at a pH of 9.4 (SNOWTEX MP-1040, Nissan Chemical Co.). 2.5 kg of deionized water and 27 kg of 2-propanol were added to the colloidal silica solution while continually agitating the mixture with a stirrer. The ratio of 2-propanol to water was 1.24 v/v.

1.44 kg of OTES (octyltriethoxysilane) was added to the reaction mixture, and the mixture was heated to about 72° C. After the addition of the OTES, the agitation of the mixture continued, and the mixture was re-circulated through a homogenizer for about 8 hours. The mixture was then held in the reactor and allowed to cool to room temperature while stirring overnight. The mixture was spray dried the following day at a temperature of about 110° C. (dryer exit temperature). The inlet temperature to the dryer was 230° C. The resulting powder was collected from the cyclone collector. After drying, the powder was jet milled and packaged.

$^{29}$Si CP/MAS NMR spectra of the inventive particles described in this example (bottom spectrum) and untreated silica particles (top spectrum) are shown in FIG. 1. The change of the relative intensities of the Q3 and Q4 peaks in the spectra indicates that some of the single silanol groups present on the surface of treated silica particles are reacted with OTES. The T2 and T3 peaks in the spectrum of the treated silica are due to the Si atoms of the OTES molecules, which became immobilized on the surface of the silica particles. T3 is about 4 to about 5 times more intense that T2, suggesting that octyltrisilanols are well cross-linked on the surface.

Figure 2:
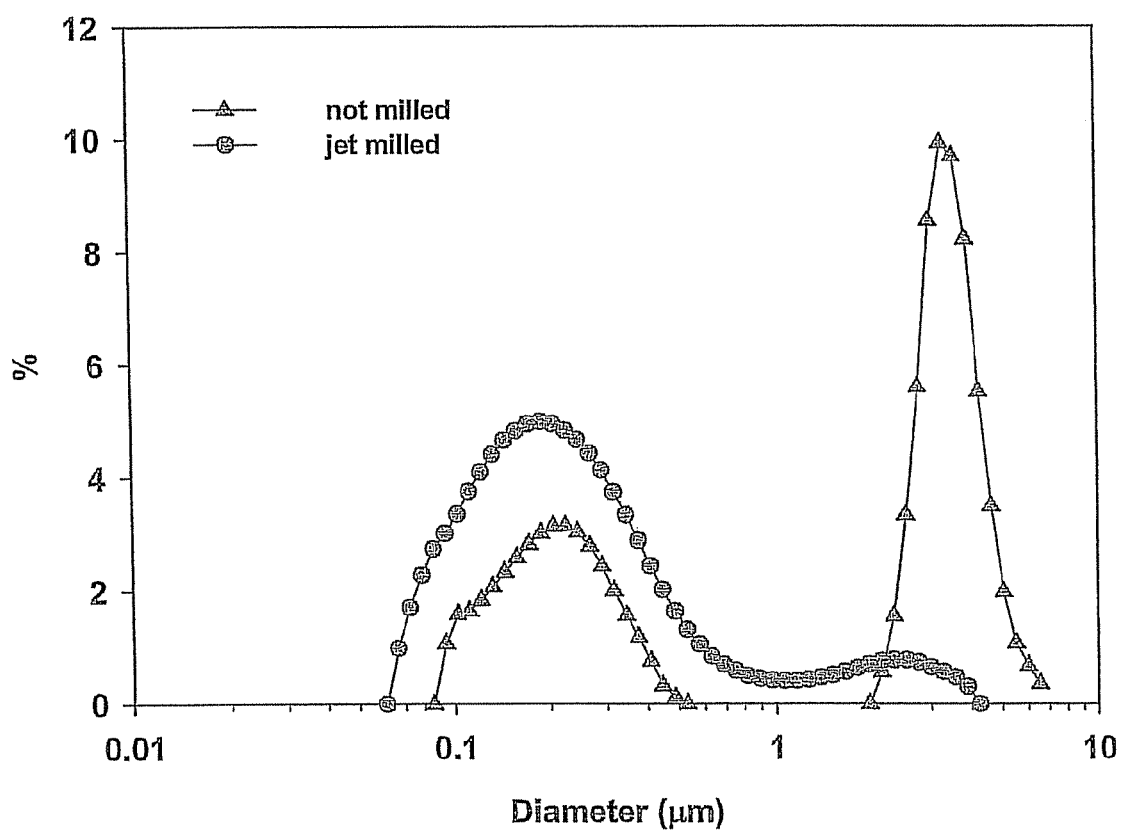
FIG. 2 is a graph of particle size distribution by volume of volume % particles versus diameter of particles (μm) for silica particles treated with OTES (octyltriethoxysilane) that have been jet milled and silica particles treated with OTES that have not been jet milled.

The effect of jet milling on the agglomerate size distribution of the inventive particles described in this example is shown in FIG. 2. As is apparent from FIG. 2, jet milling results in significantly less agglomerated material, which is preferred for toner applications.

The amount of extractable carbon was determined by extracting 0.5-2 g treated silica with 100 ml toluene and boiling for three hours using the soxhlet method.

The toner was formulated by mixing 4 wt. % of the treated silica particles in a laboratory blender with a pulverized styrene acrylate black toner free of any external additives. The average diameter of toner particles was 9 μm. The toner was developed by rolling for 30 minutes at a 2/98 wt. % toner/carrier ratio in glass jars. The carrier was 70 μm Cu—Zn ferrite coated with silicone resin. Samples were conditioned in a standard humidity chamber at either a high humidity and high temperature (30° C. and 80% relative humidity) or at a low humidity and low temperature (18° C. and 15% relative humidity) overnight. Tribocharge measurements were done using a Vertex T-150 tribo charger.

Free flow was calculated using a perforated grounded metal role tube by measuring the amount of toner discharged from the tube upon rotation. Measurements were taken after 30, 60, and 90 seconds, which were then averaged. The role tube was 25 mm in diameter, 350 mm in length, had seven 0.5 mm discharge holes, and was rotated at 30 rpm. The initial charge to the tube was 40 g.

The properties of the treated silica particles are shown in Table 1.

TABLE 1

| | |
|---|---|
| Carbon content (wt. %) | 2.7 |
| Carbon content after extraction (wt. %) | 1.78 |
| BET surface area (m$^2$/g) | 28 |
| Tap density (3000 taps) (g/l) | 257 |
| Tribocharge at high humidity & temperature (μC/g) | −13 |
| T3:T2 ratio | 4.7 |
| Tribocharge at low humidity & temperature (μC/g) | −36 |
| Free flow (wt. % loss) | 1.57 |

EXAMPLE 2

This example illustrates the preparation of hydrophobic metal oxide particles by treating colloidal silica particles with an alkoxysilane compound.

The reactor was charged with 48.3 kg of 40 wt. % colloidal silica in an aqueous solution at a pH of 9.4 (SNOWTEX MP-1040, Nissan Chemical Co.). 10.1 kg of deionized water and 44.7 kg of 2-propanol were added to the colloidal silica solution while continually agitating the mixture with a stirrer. The ratio of 2-propanol to water was 1.45 v/v.

1.78 kg of OTES was added to the reaction mixture and the mixture was heated to about 65° C. After the addition of the OTES, the agitation of the mixture continued, and the mixture was re-circulated through a homogenizer for about 7 hours. The mixture was then held in the reactor and allowed to cool to room temperature while stirring overnight. The mixture was spray dried the following day at a temperature of about 115° C. (dryer exit temperature). The inlet temperature to the dryer was 230° C. Composition 2A was dried in a cyclone drier, and composition 2B was dried in a baghouse drier. After drying, the powder was jet milled and packaged.

The amount of extractable carbon and tribocharge were measured as described in Example 1 for each of compositions 2A and 2B. The pour density was determined by obtaining a sample of the treated silica particles of composition 2A, pouring the treated silica particles into a calibrated container, and weighing them.

The properties of the treated silica particles are shown in Table 2.

TABLE 2

| | Composition 2A | Composition 2B |
|---|---|---|
| Carbon content (wt. %) | 2.41 | 2.07 |
| Carbon content after extraction (wt. %) | 1.83 | 1.79 |
| Pour density (g/l) | 234 | not determined |
| Tribocharge at high humidity & temperature (μC/g) | −18 | −19 |
| Tribocharge at low humidity & temperature (μC/g) | −38 | −45 |

EXAMPLE 3

This example illustrates the preparation of hydrophobic metal oxide particles by treating colloidal silica particles with an alkoxysilane compound.

A reactor (compositions 3A-3E) or a 3 L 3-neck flask (composition 3F) was charged with 40 wt. % colloidal silica in an aqueous solution at a pH of about 9 to about 10 (SNOWTEX XL, Nissan Chemical Co.) in the amount indicated in Table 3. Deionized water and 2-propanol were added to the colloidal silica solution while continually agitating the mixture with a stirrer.

OTES alone or both OTES and APS ((3-aminopropyl)triethoxysilane) were added to the reaction mixture, and the mixture was heated to about 68° C. to about 72° C. After the addition of the OTES alone or both OTES and APS, the agitation of the mixture continued, and the mixture was re-circulated through a homogenizer for about 5 hours to about 9 hours. The mixture was then held in the reactor or flask and allowed to cool to room temperature while stirring overnight. The mixture was spray dried the following day at a temperature of about 118° C. to about 127° C. (dryer exit temperature). The inlet temperature to the dryer was 235° C. After drying, the resulting powder was jet milled and packaged. Compositions 3B and 3D were dried in a cyclone drier, and compositions 3C and 3E were dried in a baghouse drier. Composition 3F was dried in an oven at 120° C.

The amount of extractable carbon, tribocharge, and free flow of each composition were measured as described in Example 1. The pour density of composition 3A was measured as described in Example 2.

The properties of the treated silica particles are shown in Table 3.

TABLE 3

| | Comp. 3A | Comp. 3B | Comp. 3C | Comp. 3D | Comp. 3E | Comp. 3F |
|---|---|---|---|---|---|---|
| Silica (kg) | 39 | 60.3 | 60.3 | 35.7 | 35.7 | 0.9 |
| OTES (kg) | 2.92 | 3.51 | 3.51 | 1.83 | 1.83 | .052 |
| APS (kg) | — | — | — | 0.283 | 0.283 | .0024 |
| IPA/water ratio (v/v) | 1.25 (2.9 kg water, 24.2 kg IPA) | 0.72 (30 kg water, 37.5 kg IPA) | 0.72 (30 kg water, 37.5 kg IPA) | 0.74 (30 kg water, 30.1 kg IPA) | 0.74 (30 kg water, 30.1 kg IPA) | — (750 g water, 750 g IPA) |

TABLE 3-continued

|  | Comp. 3A | Comp. 3B | Comp. 3C | Comp. 3D | Comp. 3E | Comp. 3F |
|---|---|---|---|---|---|---|
| Carbon content (wt. %) | 3.12 | 2.55 | 2.3 | 4.3 | 3.03 | 4.2 |
| Carbon content after extraction (wt. %) | 2.76 | 2.5 | 2.3 | 2.51 | 2.41 | 3.31 |
| BET surface area ($m^2/g$) | 45.9 | — | — | — | — | — |
| Pour density (g/l) | 230 | — | — | — | — | — |
| Tap density (g/l) | — | 269 | 254 | — | — | — |
| Tribocharge at high humidity & temperature ($\mu C/g$) | −19 | −24 | −26 | −11 | −16 | −17 |
| Tribocharge at low humidity & temperature ($\mu C/g$) | −44 | −59 | −58 | −16 | −21 | −31 |
| Free flow (wt. % loss) | 1.88 | 4.42 | 4.04 | 4.6 | 4.57 | — |

EXAMPLE 4

This example illustrates the preparation of hydrophobic metal oxide particles by treating colloidal silica particles with an alkoxysilane compound.

A 500 ml 3-neck round bottom flask with an overhead stirring motor and condenser was charged with 137 g of 40 wt. % colloidal silica in an aqueous solution at a pH of 9.2 (SNOWTEX YL, Nissan Chemical Co.). 87 g of 2-propanol was added to the colloidal silica solution while continually agitating the mixture with a stirrer.

6.2 g of OTES was added to the reaction mixture, and the mixture was heated to about 70° C. for about 3.5 hours. The mixture was then held in the flask and allowed to cool to room temperature. The mixture was transferred to a Pyrex tray and dried at a temperature of about 120° C.

The tribocharge and free flow of the resulting treated silica particles were measured as described in Example 1.

The properties of the treated silica particles are shown in Table 4.

TABLE 4

| Tribocharge at high humidity & temperature ($\mu C/g$) | −20 |
|---|---|
| Tribocharge at low humidity & temperature ($\mu C/g$) | −60 |
| Free flow (wt. % loss) | 1.2 |

EXAMPLE 5

This example illustrates the preparation of hydrophobic metal oxide particles by treating two different types of colloidal silica particles with an alkoxysilane compound.

A 500 ml 3-neck round bottom flask with an overhead stirring motor and condenser was charged with either 100 g of 40 wt. % colloidal silica in an aqueous solution at a pH of 9.2 (SNOWTEX XL, Nissan Chemical Co.) to which 50 ml of deionized water and 65 g of 2-propanol were added, or 75 g of 40 wt. % colloidal silica in an aqueous solution (NYACOL9950, Eka Chemicals), to which 75 ml of deionized water and 65 g of 2-propanol were added. Both compositions were continually agitated with a stirrer.

5.8 g of OTES was added to each reaction mixture. The pH of the composition containing the SNOWTEX silica was 10.1, and the pH of the composition containing the NYACOL9950 silica was 9.7. The mixtures were heated to about 70° C. for about 5.5 hours. The mixtures were allowed to cool to room temperature, then dried in an oven at a temperature of about 125° C. The dried mixtures were then milled using an IKA A 11 laboratory grinder.

The amount of extractable carbon and free flow of each composition were measured as described in Example 1.

The properties of the treated silica particles are shown in Table 5.

TABLE 5

|  | SNOWTEX XL silica | NYACOL9950 silica |
|---|---|---|
| Carbon content (wt. %) | 3.9 | 3.4 |
| Carbon content after extraction (wt. %) | 3.7 | 3.4 |
| BET surface area ($m^2/g$) | 49 | 54 |
| T3:T2 ratio | 2.6 | 5.2 |
| Free flow (wt. % loss) | 2.5 | 1.9 |

COMPARATIVE EXAMPLE 6

This example illustrates the preparation of hydrophobic metal oxide particles by treating colloidal silica particles with an alkoxysilane compound.

A 500 ml 3-neck round bottom flask with an overhead stirring motor and condenser was charged with 113 g of 35 wt. % colloidal silica in an aqueous solution (PL-8L, Fuso Co.). 37 ml of deionized water and 65 g of 2-propanol were added to the colloidal silica solution while continually agitating the mixture with a stirrer.

4.5 g of OTES was added to the reaction mixture. The pH of the reaction mixture was about 7.5. The mixture was heated to about 70° C. for about 5.5 hours. The mixture was allowed to cool to room temperature, then dried in an oven at a temperature of about 125° C. The dried mixture was then milled using an IKA A 11 laboratory grinder.

The amount of extractable carbon and free flow of the resulting treated silica particles were measured as described in Example 1.

The properties of the treated silica particles are shown in Table 6.

TABLE 6

| Carbon content (wt. %) | 0.27 |
|---|---|
| Free flow (wt. % loss) | 0.6 |
| T3:T2 ratio | Not detected |

As is apparent from the data presented in Table 6, the carbon content of the treated particles was very low and the T3:T2 ratio could not be measured, indicating that treatment was unsuccessful.

EXAMPLE 7

This example illustrates the preparation of hydrophobic metal oxide particles by treating colloidal silica particles with an alkoxysilane compound.

Three different compositions containing hydrophobic colloidal silica particles were prepared as described herein. The reactor was charged with 40 wt. % colloidal silica in a basic aqueous solution (Nissan Chemical Co.) in the amounts indicated in Table 7. Deionized water and 2-propanol (IPA) were added to the colloidal silica solutions while continually agitating the mixtures with a stirrer in the amounts indicated in Table 7.

OTES was added to the reaction mixtures in the amounts indicated in Table 7, and the mixtures were heated to about 64° C. After the addition of the OTES, the agitation of the mixtures continued, and the mixtures were re-circulated through a homogenizer for about 8-9 hours. The mixtures were then held in the reactor and allowed to cool to room temperature while stirring overnight. The mixtures were spray dried the following day at a temperature of about 119° C. to about 125° C. (dryer exit temperature). The inlet temperature to the dryer was 235° C. The powder was collected from the cyclone collector. After drying, the powder was jet milled and packaged.

The properties of the treated silica particles are shown in Table 7.

TABLE 7

| Composition | Silica | IPA/water ratio (v/v) | OTES (kg) | Tap Density (3000 taps) (g/l) |
|---|---|---|---|---|
| 7A | 40 kg SNOWTEX XL | 1.38 (0.8 kg water, 27.1 kg IPA) | 2.3 | 271 |
| 7B | 39 kg SNOWTEX MP-1040 | 1.68 (0.8 kg water, 32.1 kg IPA) | 1.47 | 265 |
| 7C | 79.1 kg SNOWTEX XL | 0.75 (40.9 kg water, 51.5 kg IPA) | 4.65 | 220 |

EXAMPLE 8

This example illustrates the preparation of hydrophobic metal oxide particles by treating colloidal silica particles with an alkoxysilane compound.

A 5 L 3-neck round bottom flask with an overhead stirring motor and condenser was charged with 1829 g of 41 wt. % colloidal silica in an aqueous solution stabilized with NaOH (NEXSIL 86, Eka Chemicals). 895 g of deionized water and 1136 g of 2-propanol were added to the colloidal silica solution while continually agitating the mixture with a stirrer.

103.7 g of OTES was added to the reaction mixture, and the mixture was heated to about 70° C. for about 6 hours. The mixture was then held in the flask overnight and allowed to cool to room temperature. The mixture was agitated to homogenize it, then the solid phase was separated by centrifugation and dried at a temperature of about 60° C. overnight, then again at a temperature of about 120° C. overnight. After drying, the resulting powder was jet milled and packaged.

The tap density of the colloidal silica particles, after 0, 300, 600, 1250, and 3000 taps, is shown in Table 8.

TABLE 8

| Tap Density (0 taps) (g/l) | 214 |
|---|---|
| Tap Density (300 taps) (g/l) | 277 |
| Tap Density (600 taps) (g/l) | 287 |
| Tap Density (1250 taps) (g/l) | 296 |
| Tap Density (3000 taps) (g/l) | 299 |

COMPARATIVE EXAMPLE 9

This example illustrates the tap density of hydrophobic fumed silica particles.

The tap density of commercially available fumed silica particles treated with OTES (AEROSIL R 805, Degussa) was measured after 0, 300, 600, 1250, and 3000 taps with a tap volumeter.

The tap density of the fumed silica particles is shown in Table 9.

TABLE 9

| Tap Density (0 taps) (g/l) | 51 |
|---|---|
| Tap Density (300 taps) (g/l) | 51 |
| Tap Density (600 taps) (g/l) | 55 |
| Tap Density (1250 taps) (g/l) | 59 |
| Tap Density (3000 taps) (g/l) | 63 |

EXAMPLE 10

This example illustrates the effect of jet milling a powder comprising hydrophobic metal oxide particles on pour density.

The reactor was charged with 40 wt. % colloidal silica in a basic aqueous solution (Nissan Chemical Co.) in the amounts indicated in Table 10. Deionized water and 2-propanol (IPA) were added to the colloidal silica solutions while continually agitating the mixtures with a stirrer in the amounts indicated in Table 10.

OTES was added to the reaction mixtures in the amounts indicated in Table 10, and the mixtures were heated to about 65° C. to about 70° C. After the addition of the OTES, the agitation of the mixtures continued, and the mixtures were re-circulated through a homogenizer for about 8-9 hours. The mixtures were then held in the reactor and allowed to cool to room temperature while stirring overnight. The mixtures were spray dried the following day at a temperature of about 110° C. to about 125° C. (dryer exit temperature). The inlet temperature to the dryer was 235° C. The powder was collected from either the cyclone collector or the bag filter. After collection, the powder was jet milled.

The pour density was measured as described in Example 2.

The properties of the treated silica particles are shown in Table 10.

TABLE 10

| Sample | Colloidal silica particle | Water (kg) | IPA (kg) | OTES (kg) | Unmilled pour density (g/l) | Unmilled tap (3000) density (g/l) | Milled pour density (g/l) | Milled tap (3000) density (g/l) |
|---|---|---|---|---|---|---|---|---|
| 10A | 41.6 kg SNOWTEX MP-1040 | 2.5 | 27 | 1.44 | 293 | 379 | 194 | 257 |
| 10B | 39 kg SNOWTEX MP-1040 | 0.8 | 32 | 1.47 | 342 | 478 | 190 | 265 |
| 10C | 59 kg SNOWTEX MP-1040 | 31 | 38 | 1.77 | 204 | 271 | 165 | 234 |
| 10D | 40 kg SNOWTEX XL | 0.8 | 27.1 | 2.3 | 354 | 508 | 185 | 271 |
| 10E | 79 kg SNOWTEX XL | 41 | 52 | 4.65 | 206 | 265 | 150 | 220 |

As is apparent from the data presented in Table 10, the pour density of the powder is significantly reduced by jet milling.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A particle composition comprising metal oxide particles surface-treated with at least one alkoxysilane compound, which surface-treated metal oxide particles are hydrophobic, non-aggregated, and have a tap density of about 110 g/l to about 420 g/l, and a BET surface area of about 200 $m^2$/g or less, and wherein a solid-state Si nuclear magnetic resonance spectrum of the surface-treated metal oxide particles exhibits a ratio T3:T2 of about 2 or more, wherein T2 is the integrated intensity of a peak having a chemical shift in the CP/MAS$^{29}$Si NMR spectrum centered within the range of −56 ppm to −59 ppm, and wherein T3 is the integrated intensity of a peak having a chemical shift in the CP/MAS$^{29}$Si NMR spectrum centered within the range of −65 ppm to −69 ppm.

2. The composition of claim 1, wherein the at least one alkoxysilane compound is octyltriethoxysilane.

3. The composition of claim 1, wherein the metal oxide particles are treated with two alkoxysilane compounds.

4. The composition of claim 3, wherein the two alkoxysilane compounds are octyltriethoxysilane and 3-aminopropyltriethoxysilane.

5. The composition of claim 1, wherein the surface-treated metal oxide particles have an average non-agglomerated size of about 0.1 microns to about 1 micron.

6. The composition of claim 1, wherein the surface-treated metal oxide particles have a BET surface area of about 100 $m^2$/g or less.

7. The composition of claim 1, wherein the surface-treated metal oxide particles have a BET surface area of about 80 $m^2$/g or less.

8. The composition of claim 1, wherein the surface-treated metal oxide particles are in the form of a dry powder.

9. The composition of claim 8, wherein the surface-treated metal oxide particles have an average non-agglomerated size of about 0.3 microns to about 0.6 microns.

10. The composition of claim 1, wherein the metal oxide particles prior to surface treatment have a true density of about 2 g/$cm^3$ to about 2.5 g/$cm^3$.

11. A toner composition comprising toner particles and metal oxide particles surface-treated with at least one alkoxysilane compound, which surface-treated metal oxide particles are hydrophobic, non-aggregated, and have a tap density of about 110 g/l to about 420 g/l and a BET surface area of about 200 m$^2$/g or less, and wherein a solid-state Si nuclear magnetic resonance spectrum of the surface-treated metal oxide particles exhibits a ratio T3:T2 of about 2 or more, wherein T2 is the integrated intensity of a peak having a chemical shift in the CP/MAS$^{29}$Si NMR spectrum centered within the range of −56 ppm to −59 ppm, and wherein T3 is the integrated intensity of a peak having a chemical shift in the CP/MAS$^{29}$Si NMR spectrum centered within the range of −65 ppm to −69 ppm.

12. The toner composition of claim 11, wherein the at least one alkoxysilane compound is octyltriethoxysilane.

13. The toner composition of claim 11, wherein the metal oxide particles are treated with two alkoxysilane compounds.

14. The toner composition of claim 13, wherein the two alkoxysilane compounds are octyltriethoxysilane and 3-aminopropyltriethoxysilane.

15. The toner composition of claim 11, wherein the surface-treated metal oxide particles have an average non-agglomerated size of about 0.1 microns to about 1 micron.

16. The toner composition of claim 11, wherein the surface-treated metal oxide particles have a BET surface area of about 100 m$^2$/g or less.

17. The toner composition of claim 11, wherein the surface-treated metal oxide particles have a BET surface area of about 80 m$^2$/g or less.

18. The toner composition of claim 11, wherein the metal oxide particles prior to surface treatment have a true density of about 2 g/cm$^3$ to about 2.5 g/cm$^3$.

19. The toner composition of claim 11, wherein the surface-treated metal oxide particles have an average non-agglomerated size of about 0.3 microns to about 0.6 micron.

* * * * *